US012622850B2

(12) United States Patent
Vacca et al.

(10) Patent No.: US 12,622,850 B2
(45) Date of Patent: May 12, 2026

(54) USE OF ZEOLITE POWDERS IN COSMETIC FORMULATIONS

(71) Applicant: SAES GETTERS S.P.A., Lainate (IT)

(72) Inventors: Paolo Vacca, Milan (IT); Miriam Riva, Lomazzo (IT); Katarzyna Fidecka, Cantù (IT); Stefano Zilio, Bareggio (IT)

(73) Assignee: SAES Getters S.p.A., Lainate (IT)

( * ) Notice: Subject to any disclaimer, the term of this patent is extended or adjusted under 35 U.S.C. 154(b) by 0 days.

(21) Appl. No.: 19/107,730

(22) PCT Filed: Mar. 8, 2024

(86) PCT No.: PCT/EP2024/056278
§ 371 (c)(1),
(2) Date: Feb. 28, 2025

(87) PCT Pub. No.: WO2024/188901
PCT Pub. Date: Sep. 19, 2024

(65) Prior Publication Data
US 2026/0000587 A1      Jan. 1, 2026

(30) Foreign Application Priority Data
Mar. 15, 2023    (IT) ........................ 102023000004857

(51) Int. Cl.
  *A61K 8/26*        (2006.01)
  *A61Q 1/00*        (2006.01)
  *A61Q 19/00*       (2006.01)

(52) U.S. Cl.
  CPC .................. *A61K 8/26* (2013.01); *A61Q 1/00* (2013.01); *A61Q 19/00* (2013.01); *A61K 2800/5922* (2013.01); *A61K 2800/61* (2013.01)

(58) Field of Classification Search
  None
  See application file for complete search history.

(56) References Cited

U.S. PATENT DOCUMENTS

2019/0322538 A1* 10/2019 Liu ......................... C01B 39/38

FOREIGN PATENT DOCUMENTS

EP         4000397 A1      5/2022
WO    WO-2018140304 A1      8/2018

OTHER PUBLICATIONS

International Preliminary Report on Patentability issued Feb. 6, 2025 in PCT/EP2024/056278, 16 pages.
International Search Report and Written Opinion issued May 10, 2024 in PCT/EP2024/056278, 15 pages.
Svetlana Mintova et al, "Nanosized microporous crystals: emerging applications." Chemical Society Reviews, XP055445047, 2015, 44(20), pp. 7207-7233.
Written Opinion issued Nov. 25, 2024 in PCT/EP2024/056278, 6 pages.

* cited by examiner

*Primary Examiner* — Danah Al-Awadi
(74) *Attorney, Agent, or Firm* — Element IP, PLC

(57) ABSTRACT

The present invention refers to synthetic lipophilic zeolites powder for the preparation of cosmetic compositions.

9 Claims, No Drawings

USE OF ZEOLITE POWDERS IN COSMETIC FORMULATIONS

FIELD OF THE INVENTION

The present invention relates to the field of cosmetic formulation and, in particular, to the use of a zeolite powder for the preparation of a cosmetic composition.

BACKGROUND OF THE INVENTION

In the field of cosmetic formulation, one of the main demand is related to the development of active formulations that, at the same time, can ensure a good spreadability and conformability to the skin.

In order to reach the expected feeling in use related to the texture of the formulation, several approaches have been followed according to the different matrixes, formulations and final applications.

For example, in the field of non-aqueous compositions, JP87158/1998 and 194327/1998 report the possibility to incorporate a thickening polymer, soluble in a polyhydric alcohol, or silica gel in order to facilitate the application of the polyhydric alcohol to the skin.

However, considering the disclosures reported above, the use of a single thickening polymer brings to the necessity of using a great amount of such compound in order to reach the desired texture of the formulation; therefore, one of the main solutions to that is, as reported in European patent application EP0974340, the possibility to use a finely particulate of inorganic compounds.

In the field of filler compositions to be added to a cosmetic composition in order to modify specific properties such as viscosity, it is known in the art, as for example reported in International patent application WO2022146700, the possibility to employ several classes of compounds such as inorganic powders, typically titanium dioxide, calcium carbonate, zinc oxide, silica compounds, clay, mica and zeolites, or organic powders and beads such as polyethylene, polymethyl methacrylate, polyamide/Nylon-12, polyethylene terephthalate, polyurethane, polysiloxanes, commonly defined as microplastics and nanoplastics.

Zeolites can be used for different purposes exploiting for example their carrier properties, as disclosed in patent applications US20200179243 or EP1971309, their capacity to generate heat when specific formulations are in contact with water as reported in European patent application EP1186286, or to modify the viscosity of a cosmetic preparation in order to improve the feelings of smoothness and spreadibility (see for example Japanese patent application JP1985218305).

However, as also reported in the cited prior art, for cosmetics formulations which comprise zeolites, silica or different texturizing fillers, usually the use of broad particles size distribution, including nanometrics particles, is reported for an easier dispersability.

In recent years, the pollution of the ocean environment and the marine-ecosystem by microplastics and nanoplatiscs has become a big concern. In 2019 the European Commission (EC) published the "European Green Deal" which comprises a set of policy initiatives with the aim of making the European Union climate neutral in 2050 and, related to that, the EC requested to the European Chemicals Agency (ECHA) to formulate a proposal for a restriction on "intentionally added microplastics" in products such as cosmetics, detergents, and agricultural products.

In addition to that, the adoption of some classes of compounds such as silica and talc has been progressively reduced due to their toxicity for human and environment.

Therefore, according to the European Commission definition of a nano material as a material where the 50% of the particles, in the number-weighted particle size distribution, have their smallest dimension below 100 nm, cosmetic products including a reduced or null amount of plastic nano-fillers are in increasing demand.

SUMMARY

The aim of the present invention is therefore to provide cosmetic formulations free of any plastic nano-filler but having the same or better spreadability and conformability to the skin with respect to the cosmetic formulations known in the art. After extensive experimentations, the inventors of the present invention found out that by using zeolite powders the texture of a cosmetic composition, can be improved while avoiding the use of nano fillers.

Glossary

All percentages, parts and ratios are based upon the total weight of the compositions of the present invention, unless otherwise specified. The term "weight percent" or "by weight" may be also denoted as "wt %" herein.

Herein, "comprising" means that other ingredients can be added. This term encompasses the term "consisting of".

DETAILED DESCRIPTION OF THE INVENTION

Specifically, it has been surprisingly found by the inventors that, by using synthetic lipophilic zeolites with well-defined technical features in a cosmetic formulation, it is possible to obtain a good spreadability and conformability on the skin, while avoiding unpleasant color and odor deriving from starting materials.

Therefore, the present invention, refers to zeolite powders, more preferably synthetic lipophilic zeolite powders as better defined below, for cosmetic formulations or compositions free of any plastic nano-fillers.

The adjective lipophilic refers to substances able of dispersing uniformly in oily or fatty phases, without the formation of deposits or precipitates.

Object of the invention is thus the use of zeolite powders for the preparation of a cosmetic formulation as defined by appended claim 1 and preferably comprising at least a synthetic lipophilic zeolite, more preferably Linde Type A (LTA) zeolites, ZSM-5 type zeolites or mixtures thereof, wherein said zeolites are characterized by a Si/Al ratio comprised between 1.0 and 50, preferably between 1.0 and 25, a pore size comprised between 3.0 and 14 Å, an accessible area per unit volume (i.e. specific accessible area) lower than 1700 $m^2/cm^3$ ($\pm 1\%$) and a Loose Bulk Density (LBD) value comprised between 100 and 700 $kg/m^3$.

The Loose Bulk Density (LBD), defined the mass of an uncompacted sample of the material divided by the volume that the sample occupies, measured in $kg/m^3$. According to the particles shape and size, resulting LBD can be very different and it was surprisingly found by the inventors, that it can affect the texture and consistency of the final cosmetic product.

It is important to point out that the use of synthetic zeolites which, according to the present invention are characterized by a Fe (II)/(III) amount lower than 0.5% by weight, brings to several advantages for the cosmetic applications.

Specifically, contrary to "natural zeolites" which are typically characterized by the presence of common contaminants and impurities such as $Fe_2O_3$ or other metal oxides arising from natural source, the synthetic zeolites are in a purer form and, as a consequence, during the formulation further purification steps are not required. Moreover, said materials do not have the characteristic odor and color of the relative natural forms or other synthetic zeolites, with a consequent advantage for the formulation of cosmetic or skincare products which may require specific colors, odors or may have to be free from both.

Said zeolites preferably comprise sodium, potassium, calcium, or hydrogen as counter-ion at an ion exchange site of the framework structure.

In the field of filler particles, the use of surface modification can be an important factor to control the surface properties and their relative behavior when added to formulations, powder mixture, rubbers and other complex systems.

According to that, in a preferred embodiment, said zeolites are characterized by a surface functionalization realized through hydrolysis-condensation reaction with a silane suitable for the use in a cosmetic composition, such as Octyl trimethoxysilane or Caprylyl Triethoxy silane. According to said embodiment, the silane quantity is in amount comprised between 0.4 and 15% by weight with respect to the total zeolites weight.

A further feature to be considered, in order to improve the texture of a cosmetic formulation, is related to the oil absorption rate of the filler added. According to that, the zeolites herein disclosed can be further characterized by an oil absorption value comprised between 10 and 160 ml/100 g of powder, preferably between 20 and 100 ml/100 g, measured by the analytical ASTM D281, certified oil absorption method by Spatula Rub-out.

In a preferred embodiment, said zeolites are characterized by an $X_{90}$ value comprised between 0.1 μm and 30 μm, preferably comprised between 0.2 and 10 μm and a surface area comprised between 200 and 900 m²/g, preferably between 300 and 600 m²/g.

The $X_{90}$ values, which indicates the spherical diameter at which 90% of the particles in the sample are comprised in the given range on a volume basis, have been determined using the analytical protocol defined according to the method ISO 13320:2020.

The surface area has been determined by suitable gas ($CO_2$ or Ar) physisorption.

Inventors found that, in order to obtain optimal results in terms of the desired properties of the cosmetic formulation, the zeolite powders should be added to the cosmetic composition in an amount comprised between 1 and 75% by weight with respect to the total weight of the cosmetic composition; preferably in an amount comprised between 1 and 20% by weight in the case of a skincare product, and in amount comprised between 20 and 75% by weight in the case of a makeup product.

Indeed, it is finally disclosed that the synthetic lipophilic zeolite powders according to the present invention, are suitable to improve the texture performance of a skincare or a makeup composition.

Skincare or makeup compositions are as generally known to a person skilled in the art, and preferably they are preparations suitable for topical application in the form of gel, cream, ointment, powder, emulsions etc.

EXAMPLES

Hereinafter, the invention will be explained in more detail with reference to the following non-limiting examples. Modifications or variations of the embodiments here exemplified, obvious to an expert in the art, are encompassed by the appended claims.

Table 1 reports some examples according to the present invention, counter examples and their relative characterizations required for the use in a cosmetic composition. Specifically, since the color of an active ingredient is a key aspect for the formulation of a cosmetic composition, the results of a colorimetric test which allow to evaluate the intrinsic color of the zeolites are of high importance.

The color of zeolites powders is visualized and quantified by using the CIELAB color space. The 3-dimensional color space is built-up from three axes that are perpendicular to one another. The L-axis values gives the lightness: a white object has an L value of 100 and the L value of a black object is 0. The a-axis is the green-red axis and the b-axis goes from blue (−b) to yellow (+b).

Each color is thus represented by a color point (L, a, b) in the color space; L, a and b are the color coordinates of the color point.

The test is made on compressed powder in a quartz sample container, using a state-of-the-art UV-Visible spectrometer equipped with an integrating sphere in reflection mode and recording the entire visible spectrum. The L, a and b parameters have been then calculated from the resulting spectrum according to CIELAB model.

TABLE 1

| | Samples | | Counter samples | | | | |
|---|---|---|---|---|---|---|---|
| Ref. | S1 | S2 | C1 | C2 | C3 | C4 | C5 |
| Zeolites framework | ZSM-5 | LTA | HEU (natural) | ZSM-5 | ZSM-5 | ZSM-5 | ZSM-5 |
| Counter ion | H+ | Na+ | Ca+ | NH4+ | NH4+ | NH4+ | NH4+ |
| Si/Al (molar ratio) | 11.5 | 1 | 6.4 | 25 | 40 | 140 | 11.5 |
| Colorimetric test (b value) | 0.44 | 0.83 | 5.46 | 2.4 | 1.1 | 1.4 | 1.53 |
| Colorimetric test (a value) | 0.12 | 0.21 | 0.99 | 0.8 | 0.3 | 0.3 | −0.15 |
| Colorimetric test (L value) | 88.81 | 88.9 | 80.81 | 82.5 | 83.3 | 83.3 | 89.03 |

For the specific use in the cosmetic filed, it is necessary to avoid colors of the starting materials, specifically the yellowish shade, thus a combination of the L, a and b parameters which correspond to white and crystalline powders. Specifically, in order to ensure that, a b value lower than 1.0 is necessary to avoid the yellow shade of the zeolites.

According to that, it is clear that the zeolites disclosed in the present invention (samples S1-S2) ensure said characteristics, while natural zeolites such as the Heulandite type zeolite (HEU) (see C1), or synthetic zeolites with a Si/Al ratio higher than 50 (C4) or with different counter-ion (C2, C3, C5) does not fulfil the required colorimetric features.

A further aspect to be evaluate in the field of cosmetic ingredients is represented by their relative odor, which has to be neutral for the correct formulation of the final composition. According to that, the odor test is made by processing an appropriate amount of sample in a headspace vial at 80° C. and then injecting the headspace gas in a gas chromatograph equipped with a mass spectrum detector. The main VOC peaks are then quantified as ethyl acetate using an appropriate calibration and the total VOC amount from each sample is calculated.

Table 2 reports the relative results, specifically, the natural zeolite (C1) or the synthetic FAU type zeolites (C6-C7) with different Si/Al ratio present a VOC release which make them not suitable for the required application, while it is confirmed that the zeolites of the present invention (S1-S2) does not present any VOC release, thus making them texturizing starting materials which, at the same time, fulfil the required features of absence of color and odor.

TABLE 2

|  | Samples | | Counter samples | | |
| --- | --- | --- | --- | --- | --- |
| Ref. | S1 | S2 | C1 | C6 | C7 |
| Zeolites framework | ZSM-5 | LTA | HEU (natural) | FAU Y | FAU Y |
| Counter ion | H+ | Na+ | Ca+ | H+ | H+ |
| Si/Al (molar ratio) | 11.5 | 1 | 6.4 | 15 | 30 |
| Odor Test GM-MS - 80° C. (30% wt dispersion in CCT) | — | — | $2.6 * 10^{-3}$ | $3.6 * 10^{-3}$ | $9.2 * 10^{-3}$ |

The invention claimed is:

1. A method of using zeolite powders to texturize a cosmetic composition, comprising incorporating a zeolite powder in a cosmetic composition, wherein said zeolite powders comprise ZSM-5 type zeolites, Linde Type A (LTA) zeolites or a mixture thereof; said zeolite powders characterized by a) a Si/Al ratio comprised between 1.0 and 25, b) a pore size comprised between 3.0 and 14 Å and a specific accessible area lower than 1700 m²/cm³, c) a Loose Bulk Density (LBD) value comprised between 100 and 700 kg/m³, d) a Fe (II)/(III) amount lower than 0.5% by weight, and e) sodium, potassium, calcium, or hydrogen as counter-ion at an ion exchange site of a framework structure.

2. The method of claim 1, wherein the zeolites have a surface functionalization realized through hydrolysis-condensation reaction with a silane suitable for the use in a cosmetic composition.

3. The method of claim 2, wherein the silane quantity is in amount comprised between 0.4 and 15% by weight with respect to the total zeolites weight.

4. The method of claim 1, wherein said zeolites are characterized by an oil absorption value comprised between 10 and 160 ml/100 g of powder measured by the analytical ASTM D281.

5. The method of claim 1, wherein said zeolites are characterized by a $X_{90}$ value comprised between 0.1 and 30 μm, measured according to the method ISO 13320:2020.

6. The method of claim 1, wherein said zeolites are characterized by a surface area comprised between 200 and 900 m²/g.

7. The method of claim 1, wherein the zeolites are combined in an amount comprised between 1 and 75%, with respect to the total weight of the cosmetic composition.

8. The method of claim 1, wherein said cosmetic composition is a skincare composition.

9. The method of claim 1, wherein said cosmetic composition is a makeup composition.

* * * * *